(12) United States Patent
Torres

(10) Patent No.: US 11,065,143 B2
(45) Date of Patent: Jul. 20, 2021

(54) WHEELCHAIR BODY HARNESS

(71) Applicant: Edwin Torres, Bronx, NY (US)

(72) Inventor: Edwin Torres, Bronx, NY (US)

(*) Notice: Subject to any disclaimer, the term of this patent is extended or adjusted under 35 U.S.C. 154(b) by 296 days.

(21) Appl. No.: 16/184,555

(22) Filed: Nov. 8, 2018

(65) Prior Publication Data
US 2020/0146869 A1  May 14, 2020

(51) Int. Cl.
A61F 5/37 (2006.01)
A61G 5/10 (2006.01)

(52) U.S. Cl.
CPC .......... *A61F 5/3792* (2013.01); *A61F 5/3784* (2013.01); *A61G 5/10* (2013.01)

(58) Field of Classification Search
CPC ....... A61F 5/3792; A61F 5/3784; A61G 5/10; A61G 5/1091
USPC ........................................................ 280/290
See application file for complete search history.

(56) References Cited

U.S. PATENT DOCUMENTS

| | | | | |
|---|---|---|---|---|
| 3,604,750 A | * | 9/1971 | Doering | A47D 15/006 297/467 |
| 4,050,737 A | * | 9/1977 | Jordan | A47D 15/006 297/465 |
| 4,330,152 A | | 5/1982 | Legan et al. | |
| 5,426,801 A | * | 6/1995 | Klearman | A61F 5/01 128/874 |
| 5,495,621 A | | 3/1996 | Kibbee | |
| 6,042,189 A | * | 3/2000 | Wellman | A61F 5/3784 280/290 |
| 6,122,778 A | * | 9/2000 | Cohen | A62B 35/0006 182/3 |
| 7,628,157 B2 | | 12/2009 | Kosh | |

* cited by examiner

*Primary Examiner* — Kevin Hurley
*Assistant Examiner* — Felicia L. Brittman
(74) *Attorney, Agent, or Firm* — Duane Morris LLP

(57) ABSTRACT

A wheelchair body harness system and method for manufacturing such system comprising a vest portion and seat area created by a strap secured between a patient's legs. The wheelchair body harness may contain a zipper along the center of the patient's chest and abdomen area of the vest portion. Adjustable side and shoulder panels may also be included to accommodate patients of different sizes. The wheelchair body harness may contain straps and buckle members across the patient's sides and shoulders that correspond to straps and buckle members located on a wheelchair or wheelchair insert. The vest portion may contain a Velcro section on the posterior side to adhere to a Velcro back of a wheelchair or wheelchair insert. The vest portion may also contain snap parts interspersed throughout the Velcro section to snap onto mating snap parts on the Velcro back of the wheelchair or wheelchair insert.

20 Claims, 5 Drawing Sheets

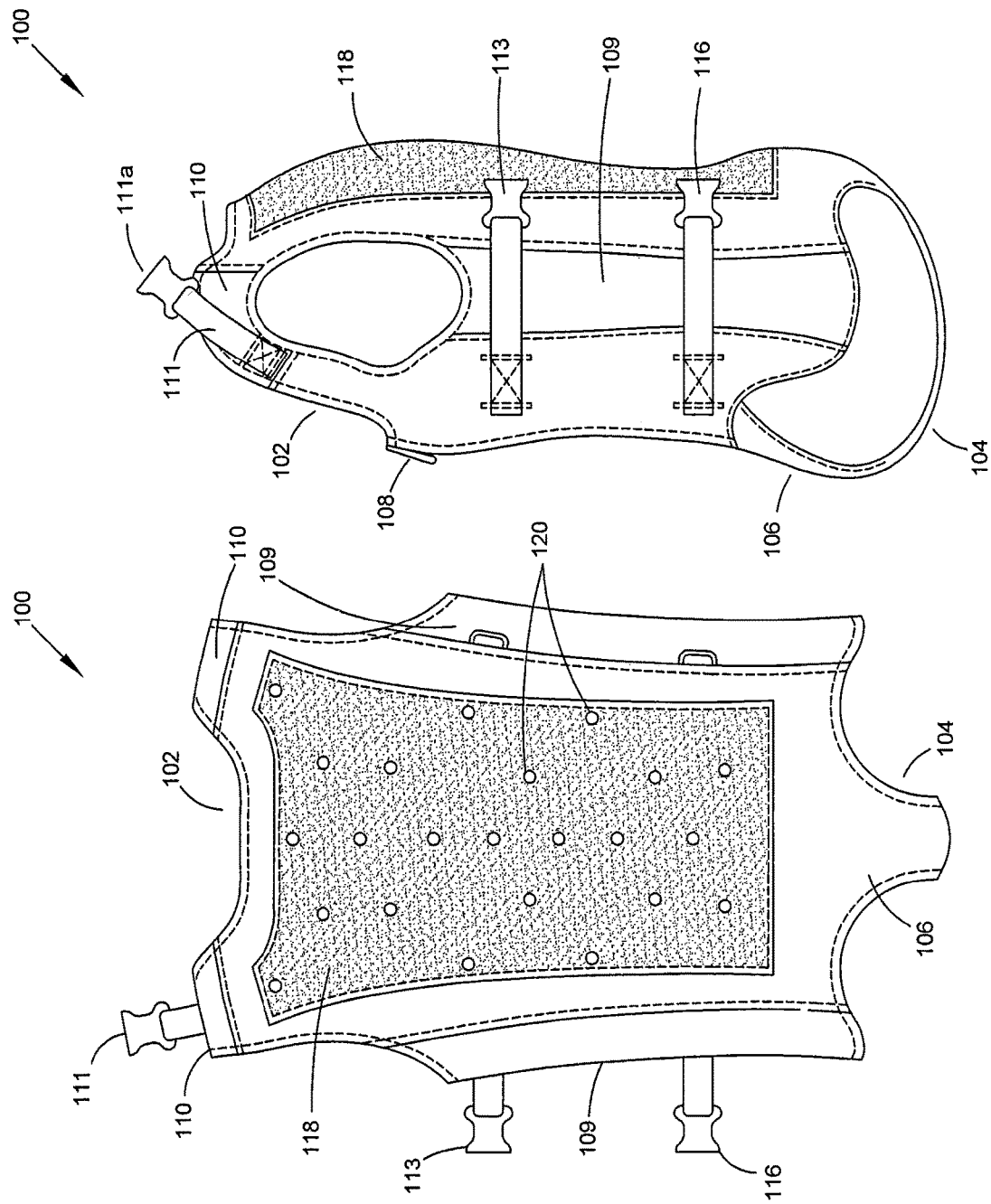

WHEELCHAIR BODY HARNESS

FIELD OF THE INVENTION

The present invention relates to a wheelchair restraint. More specifically, this present invention relates to a body harness to be used in a wheelchair restraint.

BACKGROUND OF THE INVENTION

Oftentimes individuals confined to a wheelchair have difficulty maintaining their balance while seated. In a traditional wheelchair without any form of restraint system, these individuals require adjustment or to be maneuvered by caregivers so that they remain properly seated. If they are not monitored, they tend to slouch and may even fall out of the wheelchair. Wheelchair seatbelts secure individuals to the wheelchair, however they are usually uncomfortable and can cause chaffing or rashes as a result of long-term use.

To address these problems, others have created wheelchair seatbelt covers, such as seen in U.S. patent application Ser. No. 13/087,460, published as US 2011/0254344. However, seatbelt covers still require the use of seatbelts, which may not be installed on a traditional wheelchair. Further, seatbelts need to be clicked into place, which may be difficult to accomplish by individuals in wheelchairs or by their caregivers. Additionally, seatbelt covers need to be attached to the seatbelts, which may also be difficult for individuals in wheelchairs and their caregivers, and they may slip out of place, requiring multiple adjustments. Further, some wheelchair-bound individuals require the use of adult diapers. The location of seatbelts and seatbelt covers may require the removal of the individual from the wheelchair in order to change the diaper.

SUMMARY OF THE INVENTION

The present invention overcomes these difficulties by providing a body harness which can be attached to a custom constructed wheelchair, or wheelchair insert, for a patient to wear, with a strap that is secured between the patient's legs and which can easily accommodate diaper changing. The body harness also snaps onto corresponding snaps on a wheelchair insert or on custom wheelchairs. The patient is further secured by the body harness via Velcro backing that adheres to Velcro mating material on the wheelchair insert or on custom wheelchairs. The body harness further accommodates patients of various sizes by including elastic sides.

BRIEF DESCRIPTION OF THE DRAWINGS

Additional properties and advantages of the invention are described below with reference to the accompanying schematic drawings, in which:

FIG. 2(*a*) is a posterior view, and FIG. 2(*b*) is a side view of an inventive wheelchair body harness in accordance with certain embodiments;

FIG. 3(*b*) is a perspective view of a wheelchair insert to be used with the wheelchair body harness in accordance with certain embodiments.

DESCRIPTION OF THE EMBODIMENTS

Figure 1:
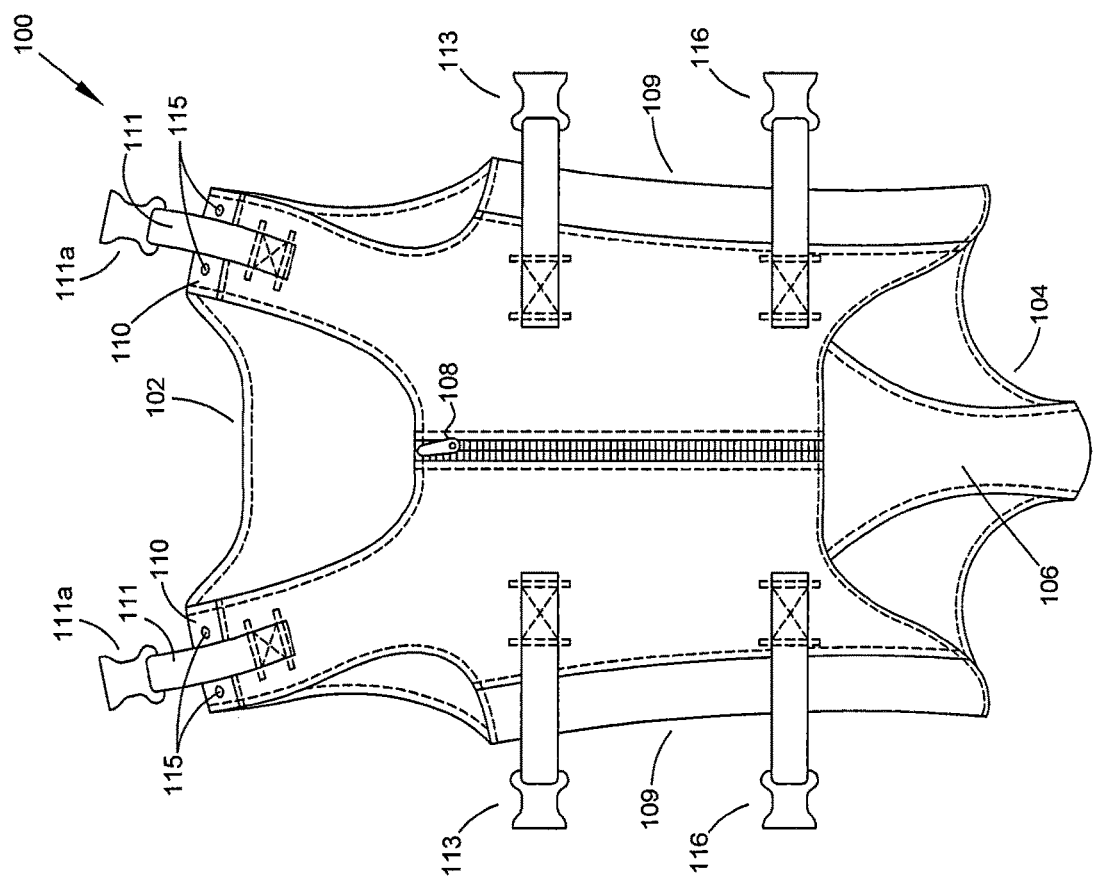
FIG. 1 is a perspective view of an exemplary embodiment of an inventive wheelchair body harness.

Identical and functionally equivalent components are usually provided with the same reference numerals in the figures.

FIG. 1 illustrates an exemplary embodiment of an inventive wheelchair body harness 100. The wheelchair body harness 100 includes a vest portion 102 and seat area 104 created by a t-shaped strap 106 that is secured between the patient's legs. The wheelchair body harness 100 may contain a zipper 108 to be fastened along the center of the patient's chest and abdomen. Elastic side and shoulder panels 109, 110, respectively, of the wheelchair body harness 100 may be made out of elastic or other elastic material to accommodate patients of different sizes. Elastic shoulder panels 110 may also separate at the patient's shoulder and be secured using snap buttons 115. To secure the wheelchair body harness 100 to a wheelchair 126 (FIG. 3) or wheelchair insert 136, the wheelchair body harness 100 may also contain straps 111 on the front of the vest portion 102 to be buckled using buckles 111*a* to the corresponding straps 112 on the wheelchair 126 or to corresponding straps 101 on the wheelchair insert 136 above the patient's shoulders. Straps 113 on the front of the vest portion 102 may be buckled to the corresponding straps 114 on the wheelchair 126 or to corresponding straps 103 on the wheelchair insert 136 on the patient's sides at the chest level. Straps 116 on the front of the vest portion 102 can be buckled via buckles 113*a* to the corresponding straps 117 on the wheelchair 126, or to corresponding straps 105 on the wheelchair insert 136, on the patient's sides at the waist level. The corresponding straps 111, 112/101, 113, 114/103, 116, and 117/105 may either have a female or male buckle member on one end that corresponds to the opposite buckle member of each corresponding strap. For example, strap 111 may contain a female buckle member 111*a* on one end that will connect with a male buckle member 112*a* on one end of strap 112. Connecting the female and male buckle members firmly secures the corresponding straps 111, 112/101, 113, 114/103, 116, and 117/105. The wheelchair body harness 100 maybe made out of canvas or other versatile materials.

FIGS. 2*a* and 2*b* show posterior and side views, respectively, of an inventive wheelchair body harness 100. The back of the wheelchair body harness 100 may contain an industrial Velcro back plate 118 with one part 120 of a snap configuration interspersed throughout the Velcro back plate 118.

Figure 3A:
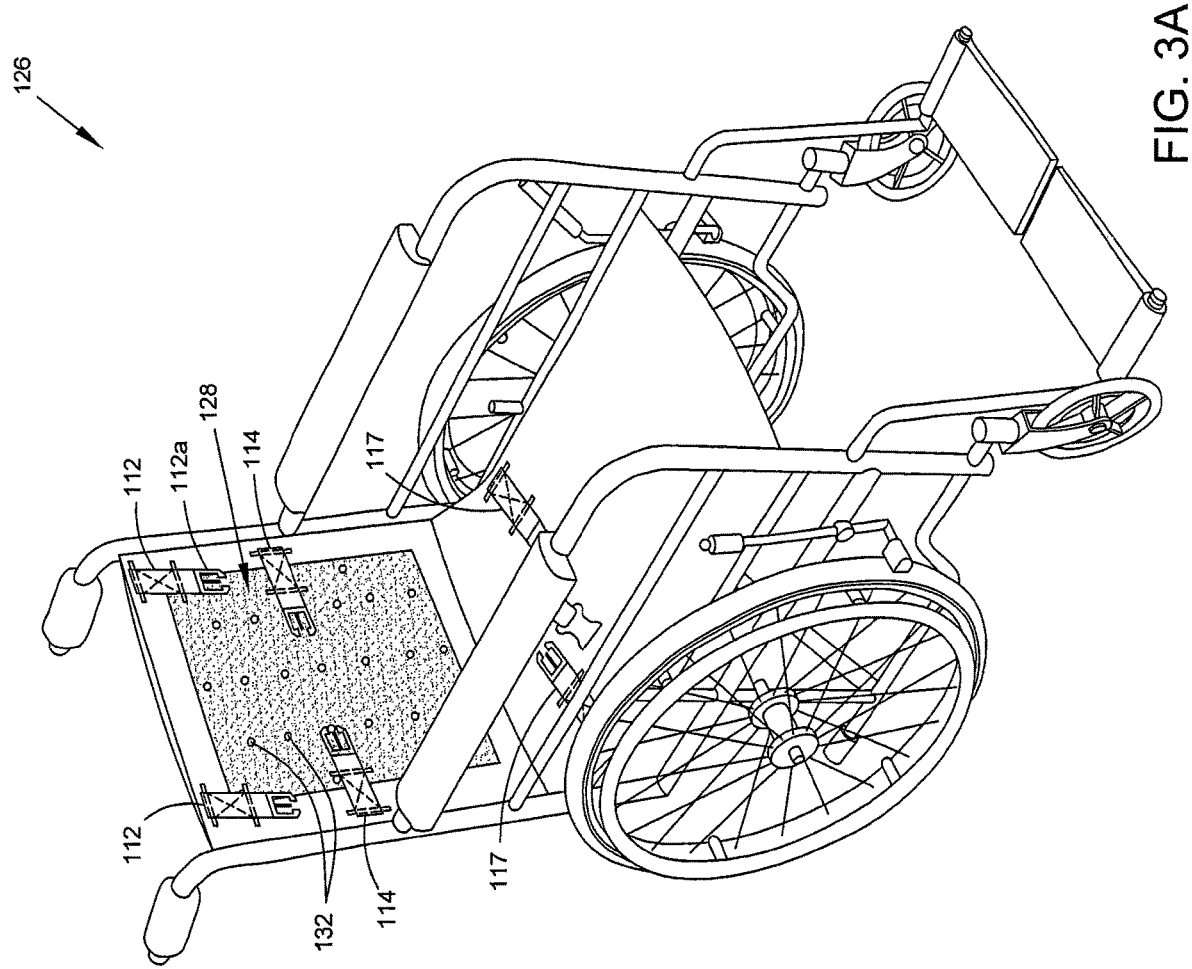
FIG. 3(*a*) is a perspective view of a wheelchair to be used with the wheelchair body harness in accordance with certain embodiments.

FIG. 3*a* shows a wheelchair 126 to be used with the wheelchair body harness 100. The wheelchair 126 may be custom-built to include straps 112, 114 and 117 to be connected with straps 111, 113 and 116 of the wheelchair body harness 100 via buckles to secure the patient at the patient's shoulders, chest and waist, respectively. The wheelchair 126 may also include an industrial Velcro back 128 which can adhere to the Velcro back plate 118 of the wheelchair body harness 100. The wheelchair 126 may also include mating snap parts 132 on the Velcro back 128 to snap into or together with the snap parts 120 of the Velcro back plate 118 of the wheelchair body harness 100.

Figure 3B:
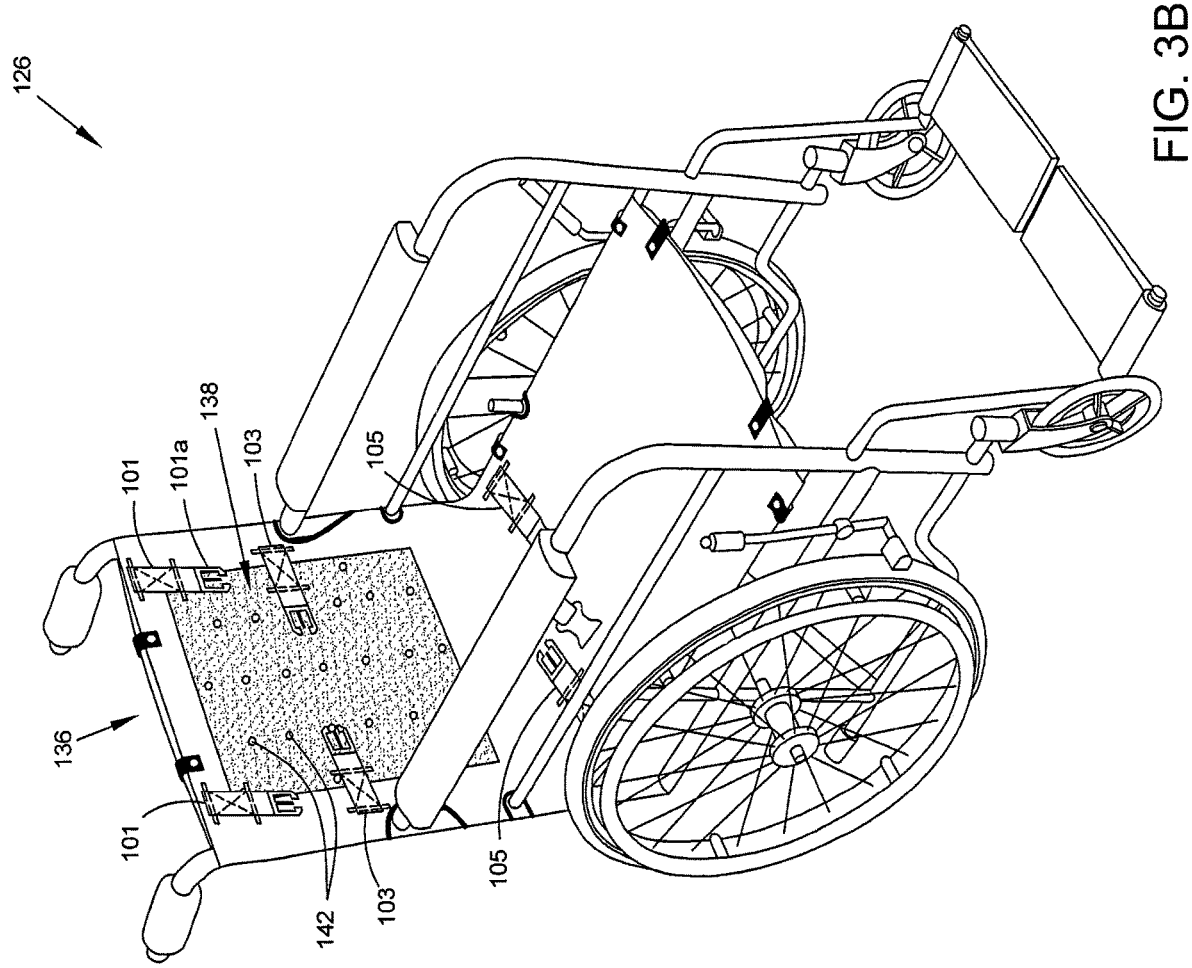

Alternatively, the wheelchair 126 may be a traditional wheelchair but a wheelchair insert 136 may be added to the wheelchair 126, as shown in FIG. 3*b*. The wheelchair insert 136 may attach to the wheelchair 126 using an adhesive or other connection such as double-sided snaps. The wheelchair insert 136 may include straps 101, 103 and 105 to correspond to straps 111, 113 and 116 of the wheelchair body harness 100 to secure the patient at the patient's shoulders, chest and waist, respectively. The wheelchair insert 136 may also include an industrial Velcro back 138 which can adhere to the Velcro back plate 118 of the wheelchair body harness 100. The wheelchair insert 136 may also include snaps 142 on the Velcro back 138 to correspond and attach to the snaps 120 of the Velcro back plate 118 of the wheelchair body harness 100.

Figure 4:
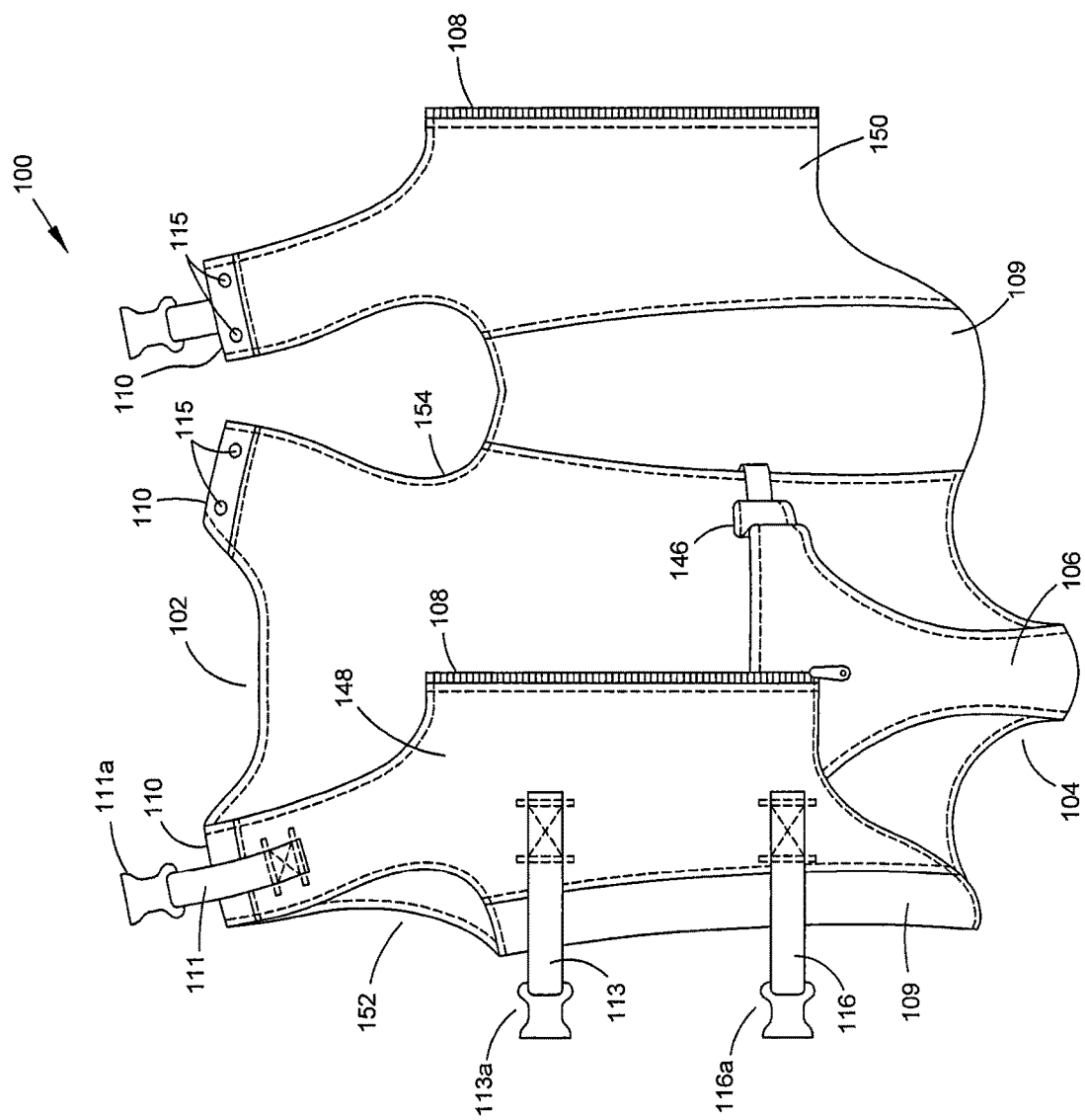
FIG. 4 is an interior view of an inventive wheelchair body harness in accordance with certain embodiments.

FIG. 4 shows an interior view of an open inventive wheelchair body harness 100. As shown, a strap 106 may be secured between the patient's legs by buckles 146 on both sides of the patient's waist in the interior of the vest portion 102 of the wheelchair body harness 100. A seat area 104 is then formed from the secured strap 106. A right flap 148 and left flap 150 of the vest portion 102 of the wheelchair body harness 100 may then be secured on top of the secured strap 106 through a zipper 108. Buckles 146 may be made of soft plastic or metal and covered by comfortable material such as felt.

In use, the wheelchair body harness 100 straps 111 will be fastened to the corresponding straps 112 via their respective buckles on a custom-built wheelchair 126 or corresponding straps 101 on a wheelchair insert 136, straps 113 will be fastened to the corresponding straps 114 on the wheelchair 126 or corresponding straps 103 on the wheelchair insert 136 and straps 116 will be fastened to the corresponding straps 117 on the wheelchair 126 or corresponding straps 105 on the wheelchair insert 136.

The Velcro back 128 of the custom-built wheelchair 126 may then adhere to the Velcro back plate 118 of the wheelchair body harness 100. Snap parts 132 on the Velcro back 128 of the custom-built wheelchair 126 may then attach to mating snap parts 120 of the Velcro back plate 118 of the wheelchair body harness 100.

Alternatively, the Velcro back 138 of the wheelchair insert 136 may then adhere to the Velcro back plate 118 of the wheelchair body harness 100. Snap parts 142 on the Velcro back 138 of the wheelchair insert 136 may then attach to mating snap parts 120 of the Velcro back plate 118 of the wheelchair body harness 100.

A patient will then be seated on the wheelchair 126, or wheelchair insert 136 that is already attached to a traditional wheelchair using an adhesive or other connection such as double-sided snaps, with strap 106 underneath the patient, between the patient's legs. The patient will insert his/her arms through arm holes 152 and 154 in the vest portion 102 of the wheelchair body harness 100. The strap 106 will then be lifted between the patient's legs and secured by buckles 146 on both sides of the patient's waist in the interior of the vest portion 102 of the wheelchair body harness 100. Buckles 146 may consist of female and male buckle members, each member may be located on respective ends of the strap 106 and in the interior of the vest portion 102 of the wheelchair body harness 100 in order to secure the strap 106 to the interior of the vest portion 102 of the wheelchair body harness 100. The right flap 148 and left flap 150 of the vest portion 102 of the wheelchair body harness 100 are then secured on top of the secured strap 106 through zipper 108. The adjustable panels 109, 110 of the wheelchair body harness 100 can then be tightened by adjusting: corresponding straps 111, 112/101, 113, 114/103, 116, and 117/105.

If a patient's diaper needs to be changed, the button snaps 115 may be opened, zipper 108 can be unzipped and buckles 146 can be undone to place strap 106 down underneath the patient, between the patient's legs. The diaper can then be replaced and buckles 146 can be secured and the zipper closed, all of which can occur without removing the patient from the wheelchair.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A wheelchair body harness system comprising:
   a vest portion with right and left flaps, said vest portion having a zipper on an anterior side of the vest portion, a plurality of side and shoulder straps and associated buckle members attached to said straps, and a hook and loop fasteners section on a posterior side of the vest portion;
   a seat portion created from a seat strap to be located between a user's legs, said seat strap having first and second buckle members corresponding to third and fourth buckle members located on respective sides of an interior waist area of the vest portion; and
   a plurality of corresponding side and shoulder straps and buckle members attached to a wheelchair to be secured to the plurality of side and shoulder straps and buckle members of the vest portion and a hook and loop fasteners back attached to a wheelchair to adhere to said hook and loop fasteners section.

2. The system of claim 1, wherein the hook and loop fasteners section comprises snap parts interspersed throughout a hook and loop fasteners area, which snap into mating snap parts located on the hook and loop fasteners back of the wheelchair.

3. The system of claim 1, wherein the vest portion further comprises adjustable side and shoulder panels.

4. The system of claim 3, wherein the adjustable side and shoulder panels are made out of elastic.

5. The system of claim 3, wherein the adjustable side and shoulder panels may be tightened by adjusting the plurality of side and shoulder straps and buckle members.

6. The system of claim 5, wherein the side and shoulder straps and buckle members are located on the anterior side of the vest portion above the vest's shoulders, on the anterior side of the vest portion on the vest's sides at a vest chest level and on the anterior side of the vest portion on the vest's sides at a vest waist level.

7. The system of claim 1, wherein the vest portion and seat portion are made out of canvas material.

8. A wheelchair body harness system comprising:
   a vest portion with right and left flaps, said vest portion having a zipper on an anterior side of the vest portion, a plurality of side and shoulder straps and associated buckle members attached to said straps, and a hook and loop fasteners section on a posterior side of the vest portion;
   a seat portion created from a seat strap to be located between a user's legs, said seat strap having first and second buckle members corresponding to third and fourth buckle members located on respective sides of an interior waist area of the vest portion; and
   a plurality of corresponding side and shoulder straps and buckle members attached to a wheelchair insert to be secured to the plurality of side and shoulder straps and buckle members of the vest portion and a hook and loop fasteners back and a hook and loop fasteners seat to adhere to said hook and loop fasteners section.

9. The system of claim 8, wherein the hook and loop fasteners section comprises snap parts interspersed throughout a hook and loop fasteners area, which snap into mating snap parts located on the hook and loop fasteners back of the wheelchair insert.

10. The system of claim 8, wherein the vest portion further comprises adjustable side and shoulder panels.

11. The system of claim 10, wherein the adjustable side and shoulder panels are made out of elastic.

12. The system of claim 10, wherein the adjustable side and shoulder panels may be tightened by adjusting the plurality of side and shoulder straps and buckle members.

13. The system of claim 12, wherein the side and shoulder straps and buckle members are located on the anterior side of the vest portion above a vest's shoulders, on the anterior side of the vest portion on the vest's sides at a vest chest level and on the anterior side of the vest portion on the vest's sides at a vest waist level.

14. The system of claim 8, wherein the vest portion and seat portion are made out of canvas material.

15. A process of manufacturing a wheelchair body harness system comprising:
creating a vest portion with right and left flaps, said vest portion having a zipper on an anterior side of the vest portion and a plurality of side and shoulder straps and associated buckle members attached to said straps, and a hook and loop fasteners section on a posterior side of the vest portion;
creating a seat strap to be located between a user's legs, said seat strap having first and second buckle members corresponding to third and fourth buckle members located on respective sides of an interior waist area of the vest portion; and
creating a wheelchair lining comprising a plurality of corresponding side and shoulder straps and buckle members to be secured to the plurality of side and shoulder straps and buckle members of the vest portion and a hook and loop fasteners back to adhere to said hook and loop fasteners section.

16. The process of claim 15, wherein the wheelchair lining is part of a custom-built wheelchair.

17. The process of claim 15, wherein the wheelchair lining is part of an insert for a traditional wheelchair.

18. The process of claim 15, further comprising
attaching snap parts to the hook and loop fasteners section, and
attaching mating snap parts on the hook and loop fasteners back of the wheelchair lining.

19. The process of claim 15, further comprising creating adjustable side and shoulder panels on the vest portion.

20. The process of claim 15, further comprising creating the vest portion and seat portion out of canvas material.

* * * * *